United States Patent [19]

Harms et al.

[11] Patent Number: 5,241,515
[45] Date of Patent: Aug. 31, 1993

[54] METHOD AND DEVICE FOR DETERMINING VARIATIONS IN THE POSITION OF A MOVABLE OBJECT BY MEANS OF ULTRASOUND

[75] Inventors: Edwin O. Harms, Groningen; Willem Prins, Eindhoven, both of Netherlands

[73] Assignee: U.S. Philips Corp., New York, N.Y.

[21] Appl. No.: 916,450

[22] Filed: Jul. 17, 1992

[30] Foreign Application Priority Data

Jul. 17, 1991 [EP] European Pat. Off. ......... 91201881.9

[51] Int. Cl.$^5$ .............................................. G01J 15/00
[52] U.S. Cl. .................................................. 367/105
[58] Field of Search ...................... 367/95, 97, 98, 105; 73/625, 626; 128/660.01

[56] References Cited

U.S. PATENT DOCUMENTS 5,068,610 11/1991 Mehlkopf et al. .................. 324/312

FOREIGN PATENT DOCUMENTS 0356629 3/1990 European Pat. Off. .

Primary Examiner—Daniel T. Pihulic
Attorney, Agent, or Firm—Jack D. Slobod

[57] ABSTRACT

Variations in the position of a part of a living object within the measurement space of magnetic resonance apparatus are determined by an ultrasound device in which bursts of ultrasonic waves having a frequency $F_{US}$ are transmitted towards the object in response to start signals generated to the repetition frequency $F_R$, and ultrasonic waves reflected by the object are received and an analog echo signal is detected which is converted into a digital echo signal made up of a sequence of echo pulses having a repetition frequency $F_{US}$. The device includes a controller for generating a time-window, for determining whether a predetermined edge of an echo pulse occurs within the time-window, and for setting the time for generating the next time-window at $1/F_R - 1/2F_{US}$ after an echo pulse has occurred within the time-window. In order to automatically generate a next time-window even in the absence of an echo pulse received in the previous time-window, an estimating circuit provides an estimated value for the time for generating the next time-window, which estimating circuit includes an envelope detector and a level detector for determining the time $t_L$ when the level of the envelope of the analog echo signal exceeds a predetermined level. The time for generating the next time-window is set at $1/F_R - 1/2F_{US}$ after the time $t_L$ if no echo pulse has occurred within the time-window.

5 Claims, 6 Drawing Sheets

METHOD AND DEVICE FOR DETERMINING VARIATIONS IN THE POSITION OF A MOVABLE OBJECT BY MEANS OF ULTRASOUND

BACKGROUND OF THE INVENTION

The invention relates to a method for determining variations in the position of a movable object, comprising the steps of:

1) generating clock pulses at a predetermined clock frequency $F_{CL}$ and a sequence of transmission start signals having a repetition frequency $F_R$ and transmitting a burst of ultrasonic waves having a frequency $F_{US}$ towards the object each time a transmission start signal has been generated;

2) starting counting clock pulses at a time that has a predetermined relationship with the time when a start signal is generated;

3) receiving ultrasonic waves having the frequency $F_{US}$ reflected by the object and forming an analog echo signal that represents the electrical equivalent of the received ultrasonic waves;

4) converting the analog echo signal into a digital echo signal comprising a sequence of echo pulses at a repetition frequency $F_{US}$, each echo pulse representing a period of the ultrasonic waves;

5) generating a time-window that has a predetermined width;

6) determining whether a predetermined edge of an echo pulse occurs within the time-window;

7) setting the time for generating the next time-window at $1/F_R - 1/2F_{US}$ seconds after an echo pulse has occurred within the time-window or at an estimated value if no echo pulse has occurred within the time-window;

8) stopping the counting of clock pulses on the occurrence of a predetermined edge of an echo pulse in the time-window.

The invention also relates to a device for determining variations in the position of a movable object, comprising:

1) a timer for generating clock pulses at a predetermined clock frequency $F_{CL}$, a sequence of transmission start signals having a repetition frequency $F_R$ and reset signals having the same repetition frequency $F_R$ and a predetermined phase relationship with the transmission start signals, the clock pulses, transmission start signals and reset signals being made available on first, second and third outputs, respectively, of the timer;

2) transmitter means having its input connected to the second output of the timer for transmitting a burst of ultrasonic waves having a frequency $R_{US}$ towards the object upon reception of a transmission start signal;

3) receiver means for receiving ultrasonic waves having the frequency $F_{US}$ reflected by the object and making available on its output an analog echo signal that represents the electrical equivalent of the received ultrasonic waves;

4) converter means for converting the analog echo signal into a digital echo signal comprising a sequence of echo pulses having a repetition frequency $F_{US}$, each echo pulse representing a period of the ultrasonic waves, the converter means having an input connected to the output of the receiver means and making available the digital echo signal on its output;

5) control means for generating a time-window that has a predetermined width, determining whether a predetermined edge of an echo pulse occurs within the time-window, setting the time for generating the next time-window at $1/F_R - 1/2F_{US}$ seconds after an echo pulse has occurred within the time-window or at an estimated value if no echo pulse has occurred within the time-window and generating a counter stop signal on the occurrence of a predetermined edge of an echo pulse in the time-window, the control means having a first input connected to the output of the converter means and an output on which the counter stop signal is made available;

6) counter means having a first input connected to the first output of the timer, a second input connected to the third output of the timer and a third input connected to the output of the control means.

A method and a device of this kind are known from EP-A-0 356 629. Such a method can be used in medicine for measuring the movements of a boundary between different tissues, e.g. the movements of a wall of an artery. It can also be used for detecting the movements of a person's chest in order to serve as a respiration sensing means.

The known method has the disadvantage that a manual start is necessary if no echo pulse has been received in the previous time-window. This means that the operator must manually activate the control means each time an echo pulse has arrived outside the time-window. If the operator fails to restart the measuring sequence without loosing too much time a serious loss of information could be the result. This is very inconvenient and can even be dangerous, e.g. when the device is used as a respiration sensor.

SUMMARY OF THE INVENTION

It is an object of the invention to provide a method and a device of the kind set forth, which automatically generates a new time-window even in the absence of an echo pulse received in the last preceding time-window, so that the measuring sequence is resumed without undue delay.

The method according the invention is characterized in that the step of estimating the value for the time for generating the next time-window comprises the steps of:

a) detecting the envelope of the analog echo signal;

b) determining the time $t_L$ when the level of the envelope exceeds a predetermined level;

c) setting the time for generating the next time-window at $1F_R - 1/2F_{US}$ seconds after the time $t_L$ if no echo pulse has occurred within the time-window.

The device according to the invention is characterized in that estimating means are provided for determining the estimated value for the time for generating the next time-window, said estimating means comprising an envelope detector for detecting the envelope of the analog echo signal and a level detector for determining the time $t_L$ when the level of the envelope exceeds a predetermined level, the control means further comprising means for setting the time for generating the next time-window at $1/F_R - 1/2F_{US}$ seconds after the time $t_L$ if no echo pulse has occurred within the time-window.

This guarantees that a next time-window is generated at about the same time it would have been generated if an echo pulse had occurred inside the previous time-window. If an echo pulse does occur within this next time-window, the acquisition of data has been interrupted for only one period of the transmission start signal repetition frequency $F_R$, that is only $1/F_R$ seconds. If no echo pulse occurs within the next time-window or in several consecutive next windows, the interruption lasts for a plurality of periods of $1/F_R$ seconds.

A preferred variant of the method according to the invention is characterized in that, if no echo pulse has occurred within the time-window, the counting of clock pulses is stopped at the time $F_L$. This method provides measuring results even if no echo pulse occurs within a plurality of consecutive time-windows.

A preferred embodiment of the device according to the invention, that is adapted to perform this variant of the method, is characterized in that the control means is adapted to generate a counter stop signal at the time $t_L$ if no echo pulse has occurred within the time window.

The device according to the invention is particularly suitable to be used in a magnetic resonance imaging or spectroscopy apparatus, e.g. to monitor the respiration of a patient being examined in such an apparatus. Such an apparatus comprises inter alia magnetic field generating means and it is important that the presence of the device does no disturb the correct operation of the apparatus. Therefore an apparatus of this kind comprising a device according to the invention is characterized in that at least the transmitter means, the receiver means and the converter means are located within an RF shield, the parts of the device which are located within the RF shield being connected to the parts outside the shield by means of connecting lines that block electrical RF signals.

BRIEF DESCRIPTION OF THE DRAWING

These and other aspects of the invention will be explained in more detail with reference to the drawing, wherein.

DETAILED DESCRIPTION OF THE PREFERRED EMBODIMENTS

Figure 1:
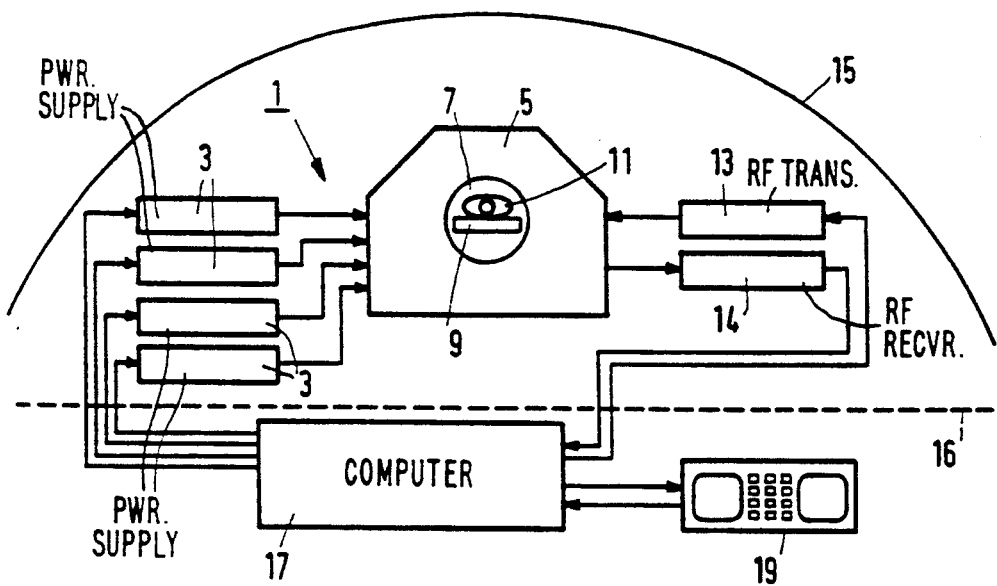
FIG. 1 very schematically shows a magnetic resonance imaging (MRI) apparatus, in which a device according to the invention can be used.

The MRI apparatus shown in FIG. 1 comprises magnetic field generating means 1 comprising a number of coils (not shown in detail) and associated power supplies 3. The coils are accommodated in a housing 5 with a bore 7 for receiving a patient support 9 with a patient 11 to be examined. An RF transmitter 13 and an RF receiver 14 are connected to selected coils (not shown) in the housing 5. This type of apparatus is well known in the art and a more detailed description can be found e.g. in EP-A-0 164 164. Because strong magnetic and RF fields are required for the operation of the apparatus, it is found useful to surround it with a magnetic shield 15 and to dispose at least the parts of the apparatus described so far behind an RF shield 16 (shown in dotted lines). Other parts of the apparatus, including a computer 17 and an operator console 19, are disposed outside the RF shield 16.

Figure 2:
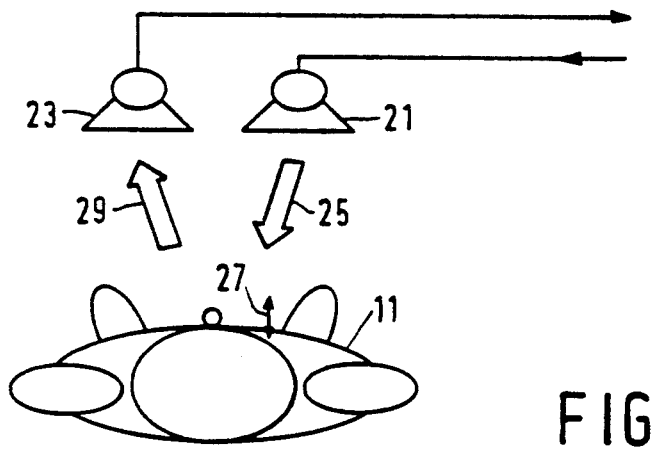
FIG. 2 shows how some parts of the device according to the invention can be positioned with respect to a patient in the apparatus shown in FIG. 1.

In many cases it is desired to acquire data relating to the physiology of the patient 11 during examination in the MRI apparatus, such as movements caused by the patient's heart beat or his breathing. Such data may be found useful in relation to the information acquired by means of the MRI examination or they may be used to reduce artifacts that could render the MRI-information less reliable. One well-known method of detecting the movements of parts of a patient, such as the heart and arteries or the chest (to detect breathing) uses the reflection of ultrasonic waves by these parts. When an ultrasonic wave is transmitted towards an object and the reflection caused by the object is received, the time that elapses between transmission and reception depends on the distance between the transmitter/receiver and the object. Consequently, if the object moves towards or away from the transmitter/receiver, the time required for the round-trip of the ultrasonic wave changes correspondingly. This phenomenon is used in known devices to observe the motion of parts of a patient, see e.g. EP-A-0 356 629. A device of this kind may comprise first and second electroacoustic transducers 21 and 23 as shown in FIG. 2. The first transducer 21 is used for transmitting a beam 25 of ultrasonic waves towards the chest of the patient 11, which moves due to breathing as indicated by the arrow 27 and the second transducer 23 is used for receiving the reflected beam of ultrasonic waves 29. It is also possible to use a single transducer for transmission and reception (not shown).

Figure 3:
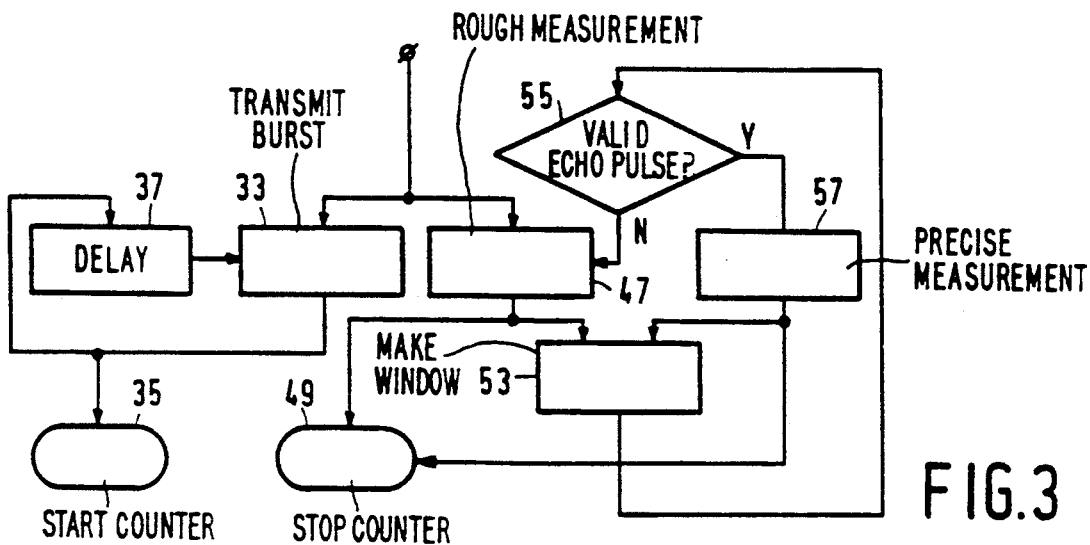
FIG. 3 is a flow chart illustrating some steps of an example of the method according to the invention.
Figure 4:
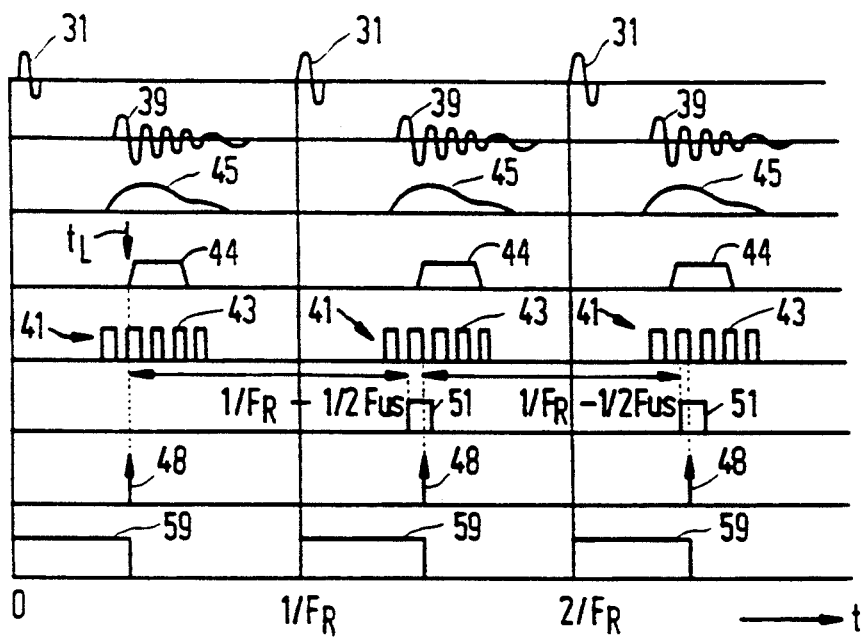
FIG. 4 is a diagram showing the timing of some signals in the method according to the invention.

FIG. 3 is a simplified flow chart in accordance with an example of the method of the present invention and FIG. 4 shows some of the signals that are generated while the method is performed. At the beginning of an examination period a transmission start signal 31 is generated, which triggers the transmission of a burst of ultrasonic waves (box 33) having a frequency $F_{US}$ towards the object to be examined, e.g. the chest of the patient 11 shown in FIG. 2. At the same time a counter starts counting clock pulses (box 35). After a delay of $1/F_R$ seconds (box 37) this process is repeated so that the transmission of bursts of ultrasonic waves is a periodic process having a repetition frequency $F_R$. The burst of ultrasonic waves is reflected by the object and the reflected waves are received at a time that depends on the distance between the object and the transducers 21,23. From the received burst of waves an analog echo signal 39 is formed, that represents the electrical equivalent of the received waves. This analog echo signal is converted into a digital echo signal 41 comprising a sequence of echo pulses 43 at a repetition frequency $F_{US}$, each echo pulse representing a period of the ultrasonic waves. Also the envelope 45 of the analog echo signal 39 and the time $t_L$ when this envelope exceeds a predetermined level are determined. This time provides a comparatively rough measurement of the time that has lapsed between the transmission of the burst and the reception of the echo (box 47). The first time an echo is received after the beginning of the examination a counter stop signal 48, which causes the counter to stop counting clock pulses, is generated at the time $t_L$ (box 49). A time-window 51 is generated (box 53) at a time $1/F_R - 1/2F_{US}$ seconds after the time $t_L$, which is the time the second of the sequence of echo pulses 43 of the next digital echo signal 41 can be expected.

After the generation of the next transmission start signal 31 this process is repeated, but now it is checked whether the digital echo signal 43 comprises a valid echo pulse 43 (box 55). A valid echo pulse is defined as an echo pulse having a leading edge that is situated within the time-window 51. Other definitions are of course also possible, e.g. an echo pulse with its trailing edge within the time-window. If a valid echo pulse 43 is found, this must be the second echo pulse of the digital echo signal 41 because the time-window 51 had been positioned at a time when this second pulse was to be expected. The leading edge of this echo pulse corresponds exactly to the second zero-crossing of the analog echo signal, which is a well-defined feature and consequently it indicates very precisely at what moment in time the echo signal arrives at the second transducer 23. The instant when the envelope of the analog echo signal exceeds a predetermined level is a much less reliable indication of this moment because the amplitude of the analog edge signal may vary considerably, e.g. as a result of variations in the acoustic coefficient of reflection of the clothing that the patient 11 is wearing. Therefore the measurement of the time that has elapsed between the generation of the transmission start signal 31 and the detection of the leading edge of a valid echo pulse 43 provides a precise measurement of the distance between the transducers and the object (box 57). The counter stop signal 48 is generated and the counter is stopped on the occurrence of the leading edge of the valid echo pulse 43 and the next time-window 51 is generated at $1/F_R - 1/2F_{US}$ seconds after this occurrence (boxes 49 and 53). If no valid echo pulse has occurred within the time-window, the rough measurement of box 47 is performed using the instant when the envelope of the analog echo signal exceed a predetermined level as described above. Signal 44 in FIG. 4 indicates when envelope 45 exceeds this predetermined level. This procedure ensures that for each burst of ultrasonic waves that is transmitted towards the object a measuring result is obtained, even though this result is less accurate when no echo pulse 43 occurs within the time-window 51. The period during which the counter is counting clock pulses is indicated at 59. The counter may start counting at the instant the transmission start signal 31 is generated as shown in FIG. 4, but is may also start at an instant which is delayed for a predetermined time with respect to the transmission start signal. In both cases the period 59 is a measure for the distance between the transducers 21,23 and the chest of the patient 11. This distance varies due to the breathing of the patient 11, so the method is suitable to be used as a respiration sensor.

Figure 5:
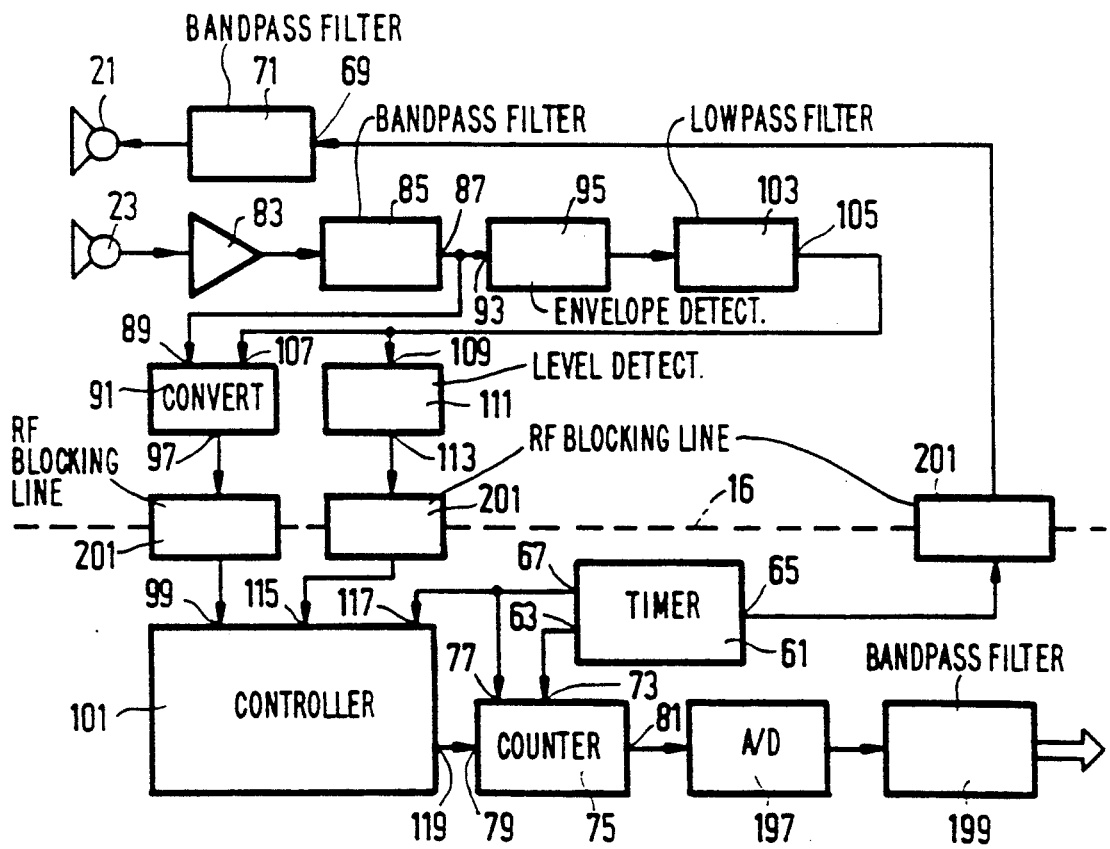
FIG. 5 is a block diagram of an embodiment of the device according to the invention.

FIG. 5 is a block diagram of an embodiment of a device for performing the method described above. This device comprises a timer 61 for generating clock pulses at a predetermined clock frequency $F_{CL}$ (e.g. 1.25 MHz), a sequence of transmission start signals 31 and reset signals having the same repetition frequency $F_R$ (e.g. 300 Hz) as the transmission start signals. Each transmission start signal may comprise a burst of one period of a signal having the frequency $F_{US}$ (e.g. 40 kHz). The clock pulses are made available on a first output 63, the transmission start signals on a second output 65 and the reset signals on a third output 67. The second output 65 is connected to the input 69 of a transmitter means which may comprise a band-pass filter 71 having a central frequency $F_{US}$ and strongly attenuating RF signals to prevent interference with the RF circuits of the MRI apparatus 1. The transmitter means also comprises the first transducer 21.

The first output 63 of the timer 61 is connected to a first input 73 of a counter 75 (to be described in more detail later with reference to FIG. 10) and the third output 67 is connected to a second input 77 of the counter. The counter 75 further comprises a third input 79, adapted to receive a counter stop signal, and an output 81. When it receives a reset signal on its second input 77, the counter 75 starts counting the clock pulses received on its first input 73. When it receives a counter stop signal on its third input 79, the counter 75 stops counting and produces a counter output signal on its output 81.

Figure 8:
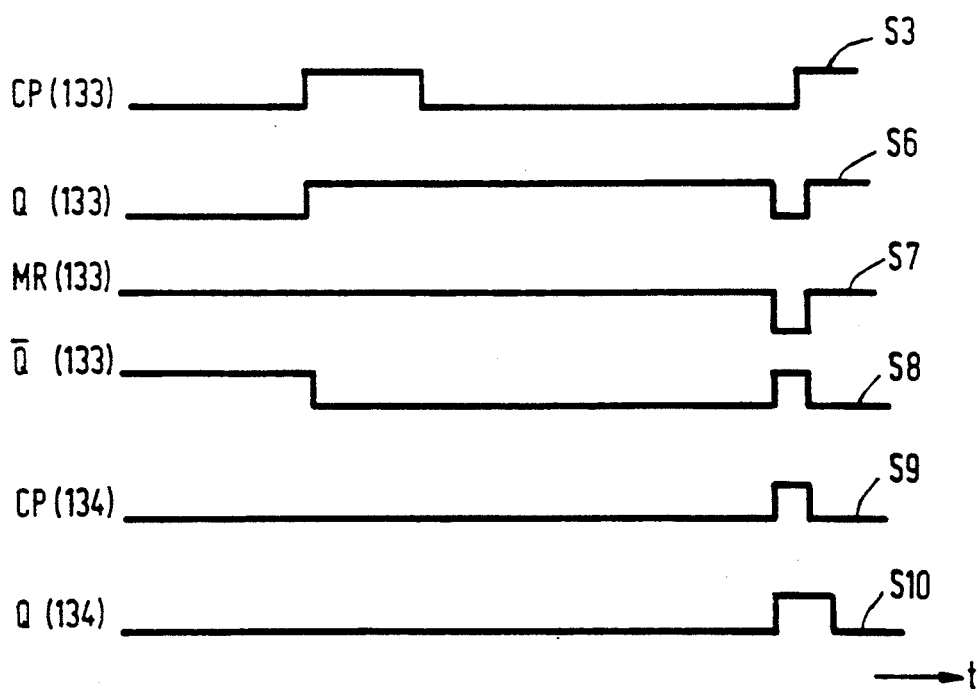

The device also comprises receiver means comprising the second transducer 23 connected to the series-connection of a pre-amplifier 83 and a band-pass filter 85 having a central frequency $F_{US}$. On the output 87 of the receiver means the analog echo signal is available. This output is connected to a first input 89 of a converter 91 and to the input 93 of an envelope detector 95. The converter 91, which will be discussed in detail later with reference to FIG. 9, converts the analog echo signal 39 into the digital echo signal 41 which is made available on its output 97 that is connected to a first input 99 of a control means or controller 101. The envelope detector 95 may be a well-known diode detector which is followed by a low-pass filter 103 having a central frequency of 25 kHz. The envelope 45 of the analog echo signal 39 is made available on the output 105 of the low-pass filter 103, which is connected to a second input 107 of the converter 91 and to the input 109 of a level detector 111. The level detector 111, which will be described in detail later with reference to FIG. 8, provides a signal on its output 113 at the time $t_L$ when the level of the envelope 45 exceeds a predetermined level. The output 113 of the level detector 111 is connected to a second input 115 of the controller 101 which also has a third input 117 connected to the third output of the timer 61 and an output 119 connected to the third input 79 of the counter 75.

Figure 6:
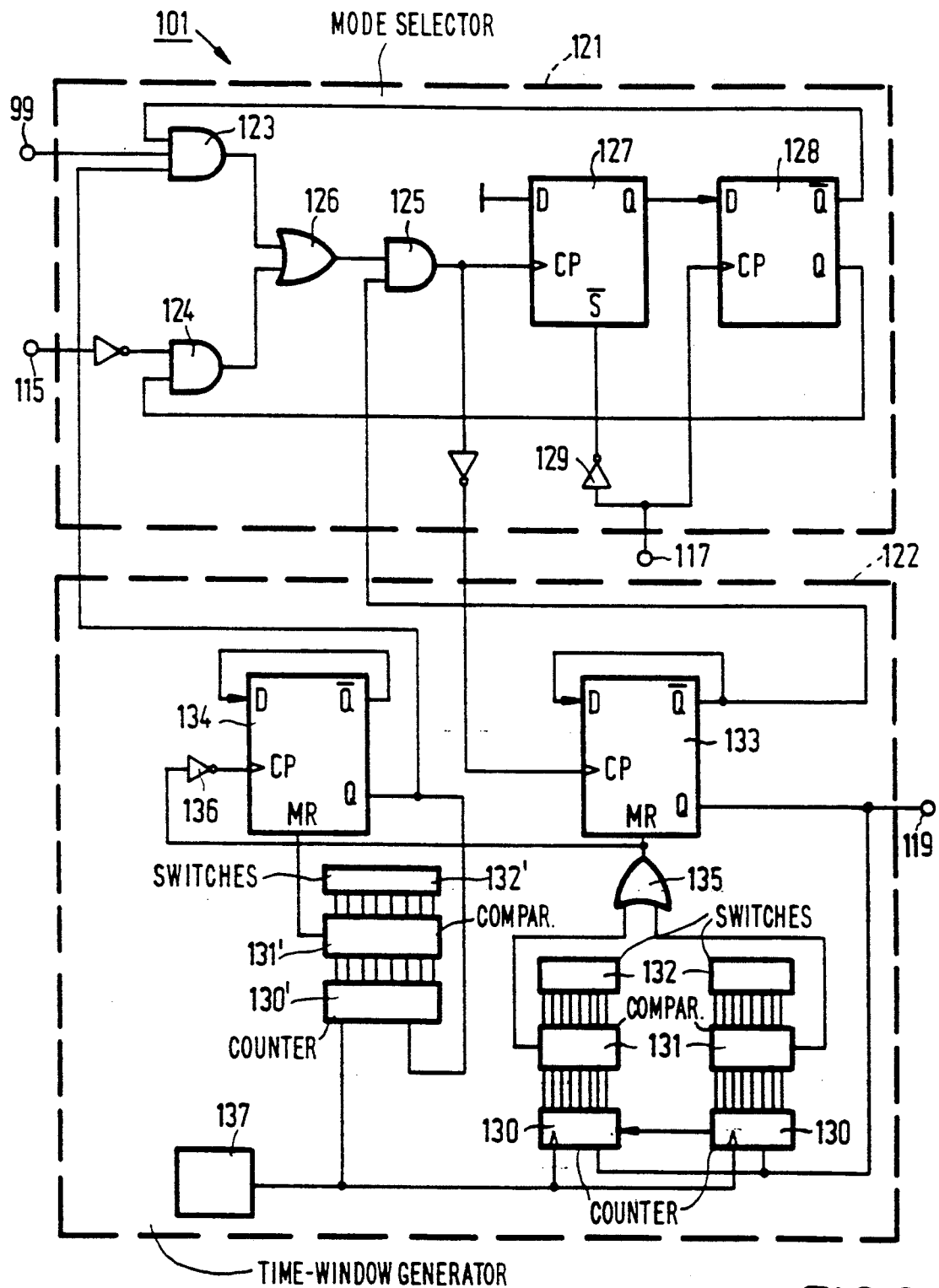
FIG. 6 is a block diagram of a part of the device shown in FIG. 5, FIGS. 7 and 8 are diagrams showing the timing of some signals in the part shown in FIG. 6, and FIGS. 9-12 show block diagrams of embodiments of various other parts of the device according to the invention.

An embodiment of the controller means 101 will now be described in some detail with reference to FIG. 6. This embodiment comprises two parts: a mode selector 121 and a time-window generator 122. The mode selector 121 comprises three AND-gates 123, 124 and 125 and an OR-gate 126. The mode selector 121 further comprises two flipflops 127,128 and an inverter 129. The time-window generator 122 comprises three counters 130,130' three comparators 131,131' with associated pre-set switches 132,132', two flipflops 133, 134, an OR-gate 135, an inverter 136 and a 10 MHz oscillator 137. The interconnection between the various components of the two parts 121, 122 and their connections to the inputs 99, 115 and 117 and the output 119 of the control means are clearly shown in FIG. 6. The operation of these circuits is self-explanatory but a brief explanation will be given with reference to FIGS. 7 and 8.

Figure 7:
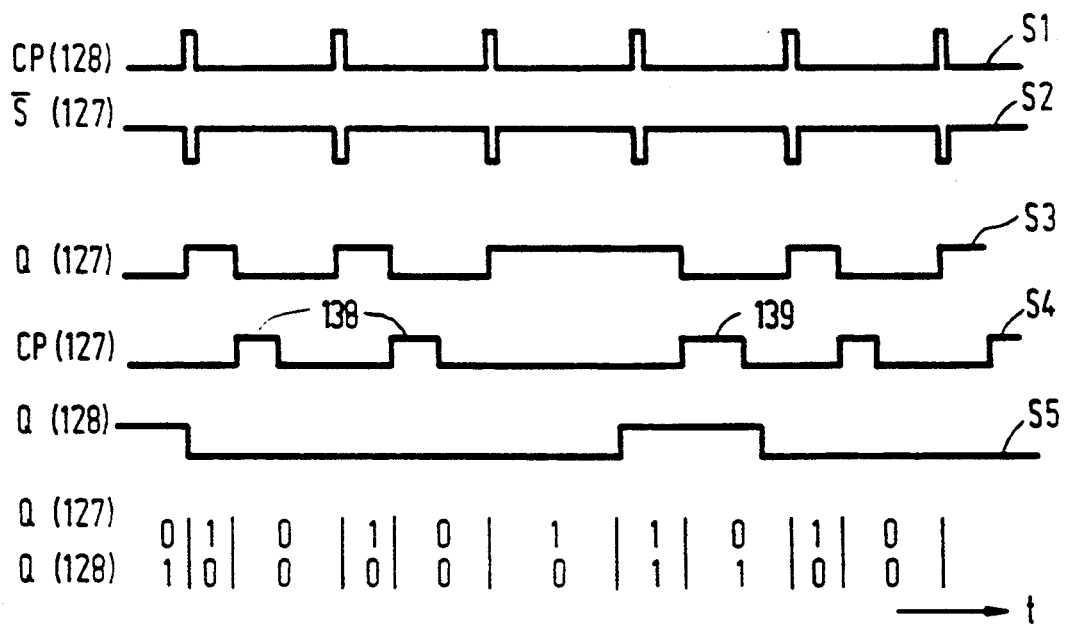

FIG. 7 shows five signals s1 . . . s5 of the flipflops 127,128 of the mode selector 121, the connections of the flipflops on which these signals appear being indicated at the left side of the figure. The signal s1 is the reset signal arriving at the third input 117 of the control means 101 and the signal s2 is the inverse of this signal. Each time a signal s2 arrives at the flipflop 127 this flipflop assumes its ground state, making Q(127) high (signal s3). The signal s4 is the output signal of the AND-gate 125 and it comprises either pulses 138 corresponding to the signal at the first input 99 of the control means 101 (if a valid echo pulse 43 has been detected) or pulses 139 corresponding to the signal at the second input 115. The arrival of the signal s4 makes the signal s3 low. If no valid echo pulse arrives, Q(128) (signal s5) is switched to its high level and the mode selector 121 waits for an envelope signal to arrive. The states of Q(127) and Q(128) are shown at the bottom of FIG. 7.

Table 1 shows the states of the mode selector 121. In this table the expression "rough detection" refers to the detection of an envelope signal 45 which provides a comparatively rough indication of the round-trip time of a burst of ultrasonic waves as explained with reference to FIGS. 3 and 4.

TABLE 1

| STATE | Q(127) | Q(128) | OPERATION |
| --- | --- | --- | --- |
| 1 | 0 | 0 | valid echo pulse just passed |
| 2 | 0 | 1 | rough detection just passed |
| 3 | 1 | 0 | waiting for valid echo pulse |
| 4 | 1 | 1 | waiting for rough detection |

When the device starts measuring, the mode selector is set into state 2. When in state 3 a valid echo pulse is detected, the mode selector switches over to state 1 and when no valid echo pulse is detected, it switches over to state 4.

FIG. 8 shows six signals s3 ... s10 of the flipflops 133.134 of the time-window generator 122, the time scale being different from the time scale of FIG. 7. On the arrival of a signal s3 (this is the same signal as the signal s3 in FIG. 7) the Q-signal s6 of the flipflop 133 is switched to a high level and the counters 130 start counting pulses from the oscillator 137. When the counters 130 reach the value preset by means of the switches 132, the comparators 131 produce a count end signal s7 that is presented, via the OR-gate 135, to the MR input of the flipflop 133. The signal s6 then assumes a low level and its inverse signal s8 assumes a high level. The signal s8 is supplied to the output 119 of the control means 101. The inverse signal s9 of the count end signal s7 is supplied to the CP input of the flipflop 134 which causes Q(134) to provide a high signal that causes the counter 130' to start counting until the value preset by means of the switch 132' (corresponding to the predetermined width of the time-window) is reached.

Table 2 shows the states of the time-window generator 122.

TABLE 2

| STATE | Q(133) | Q(134) | OPERATION |
| --- | --- | --- | --- |
| 1 | 0 | 0 | wait for startpulse |
| 2 | 0 | 1 | count the window width |
| 3 | 1 | 0 | count the delay time |
| 4 | 1 | 1 | does not exist |

In state 1 the circuit is waiting for a start pulse from the output of the gate 125. When the device starts measuring, the time-window generator is set into state 1. When a start pulse is received, the generator switches to state 3. In this state it counts till the moment for generating the next time-window ($1/F_R - 1/2F_{US}$ seconds after the start pulse has been received) has arrived. When this moment comes, the circuit switches to state 2 in which it counts till $1/F_{US}$ seconds (the predetermined width of the time-window) have elapsed. Then it switches again to state 1.

Figure 9:
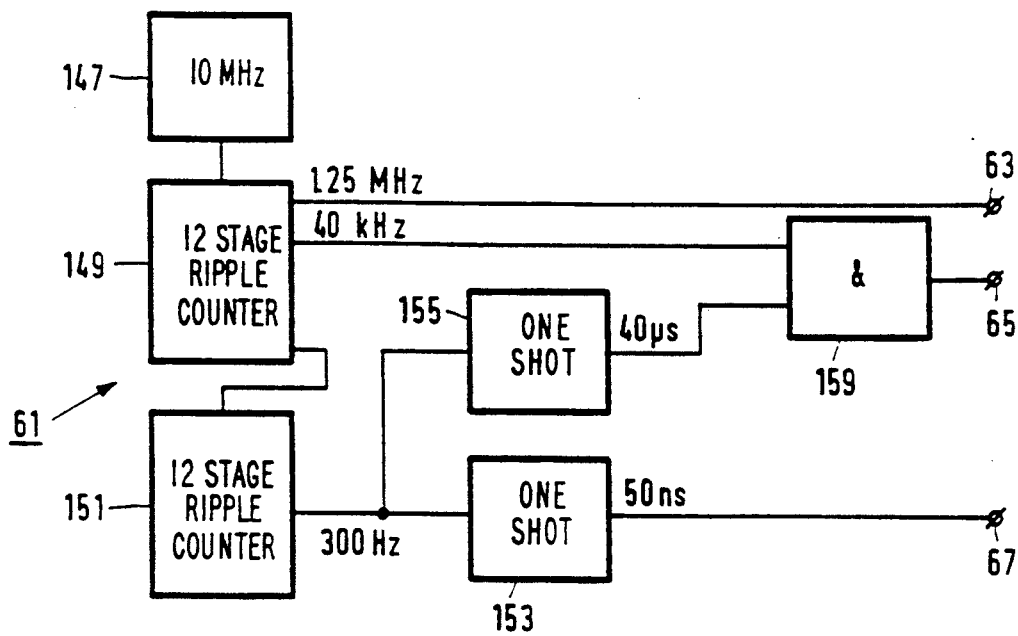

FIG. 9 shows a block diagram of an embodiment of the timer 61. This circuit comprises a 10 MHz oscillator 147 connected to a series-connection of two twelve-stage ripple counters 149 and 151. The first ripple counter 149 provides at its first output, which is connected to the first output 63 of the timer, a series of clock pulses at a clock frequency $F_{CL}$ of 1.25 MHz and at its second output a signal having a frequency of 40 kHz. The second ripple counter 151 provides at its output a 300 Hz signal which is converted by a first one-shot multivibrator 153 into a series of transmission start pulses having a length of 50 ns each and a repetition frequency $F_R$ of 300 Hz. The output of the first one-shot multivibrator 153 is connected to the third output 67 of the timer. A second one-shot multivibrator 155 converts the 300 Hz signal into a series of pulses having a length of 40 μs and a repetition frequency of 300 Hz. The output of the second one-shot multivibrator 155 is connected to a first input of an AND-gate 159 and the second output of the first ripple counter 149 is connected to the second input of this gate. At the output of the gate 159, which is connected to the second output 65 of the timer, bursts of the 40 kHz signal are produced.

Figure 10:
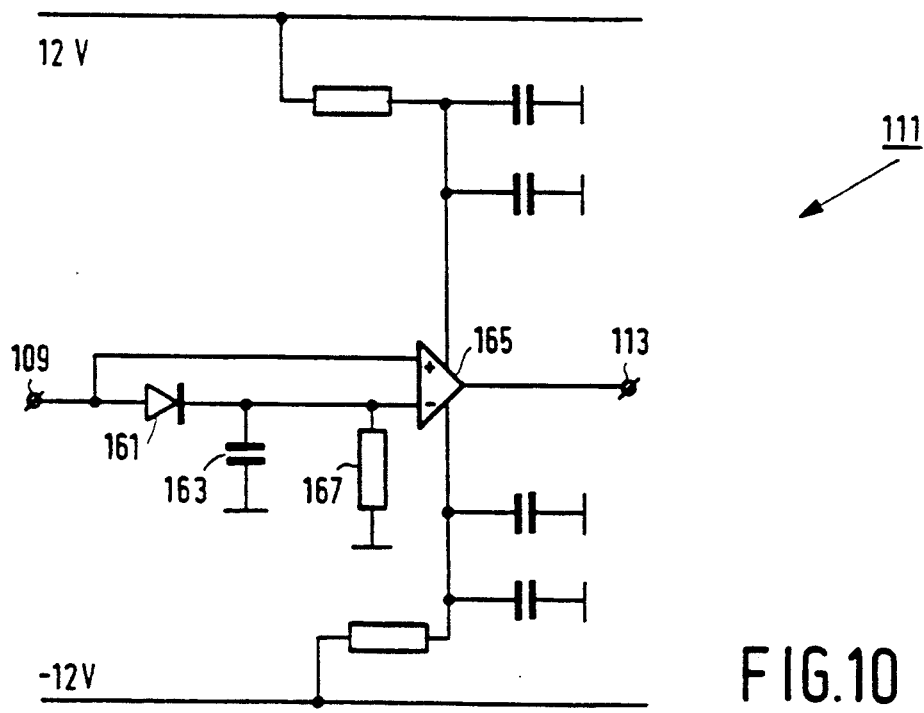

FIG. 10 shows a circuit diagram of an embodiment of the level detector 111. This circuit comprises a diode detector and a comparator. The diode detector comprises a diode 161 and a capacitor 163 and the comparator comprises a differential amplifier 165. A resistor 167 is connected in parallel to the capacitor 163 so that the detected voltage which is stored in the capacitor decreases with a time-constant that depends on the RC-product. This RC-product is chosen so that the voltage on the capacitor 163 decreases to about 0.7 times its original value in $1/F_R$ seconds. The resulting voltage is supplied to the negative input of the amplifier 165. The positive input of this amplifier is directly connected to the input 109 of the level detector 111, to which also the input of the diode detector is connected. Consequently the comparator compares the voltage of the envelope 45 with 0.7 times the voltage of the previous envelope. The output of the amplifier 165 is connected to the output 113 of the level detector 111 which consequently supplies a signal to the second input 115 of the control means 101 if the former voltage exceeds the latter.

Figure 11:
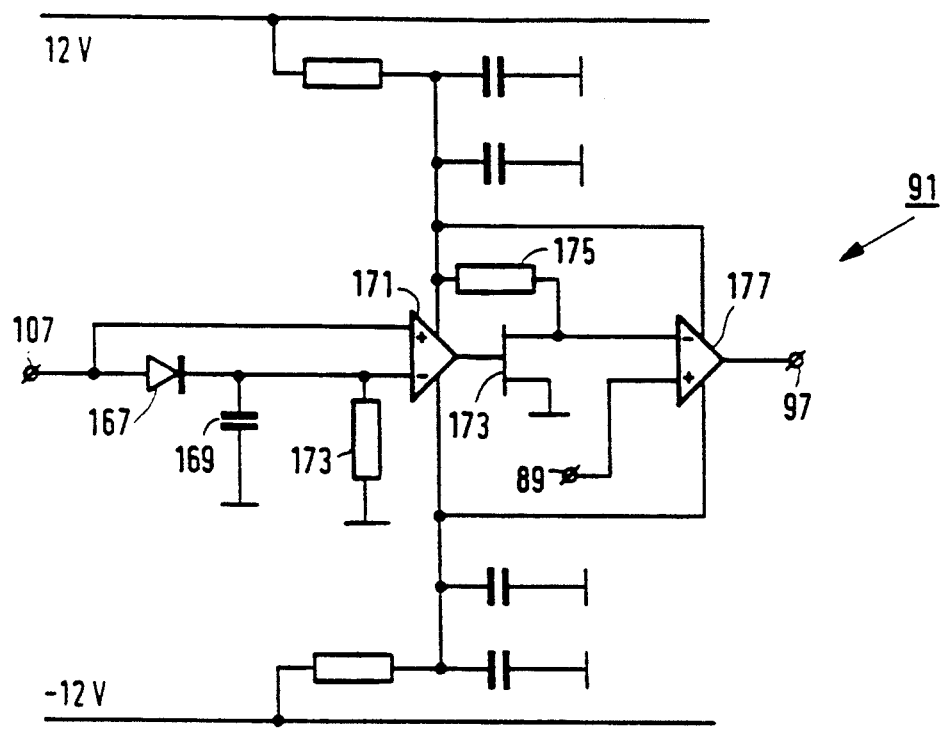

FIG. 11 shows a circuit diagram of an embodiment of the converter 91. This circuit comprises a level detector, a switch and a comparator. The construction and the operation of the level detector are substantially the same as those of the level detector 111 discussed with reference to FIG. 8. It comprises a diode 167, a capacitor 169, a differential amplifier 171 and a resistor 173. This level detector compares the level of the envelope supplied to the second input 107 with the level of the previous envelope. The RC-product of the capacitor 169 and the resistor 173 are chosen so that the detection level is 0.2 times the level of the previous reflection. The switch comprises a field-effect transistor (FET) 173 having its gate electrode connected to the output of the level detector, its drain electrode being connected, via a resistor 175, to the +12 volt supply line and its source electrode to ground. If the level detector does not produce an output signal (no reflection detected) the FET 173 is non-conducting and consequently its drain electrode is at 12 V. If a reflection is detected, the level detector produces an output signal and the FET is conducting. In that case the drain electrode is at ground potential. The comparator comprises a differential amplifier 177 having its positive input connected to the first input 89 of the converter 91, its negative input to the drain electrode of the FET 173 and its output to the output 97 of the converter. Consequently the comparator compares the analog echo signal 39 with 0 V when a reflection is detected. In that case the analog echo signal is converted into a block wave which forms the digital echo signal 41. The comparator compares with 12 V when no reflection is detected. In that case the output is zero.

Figure 12:
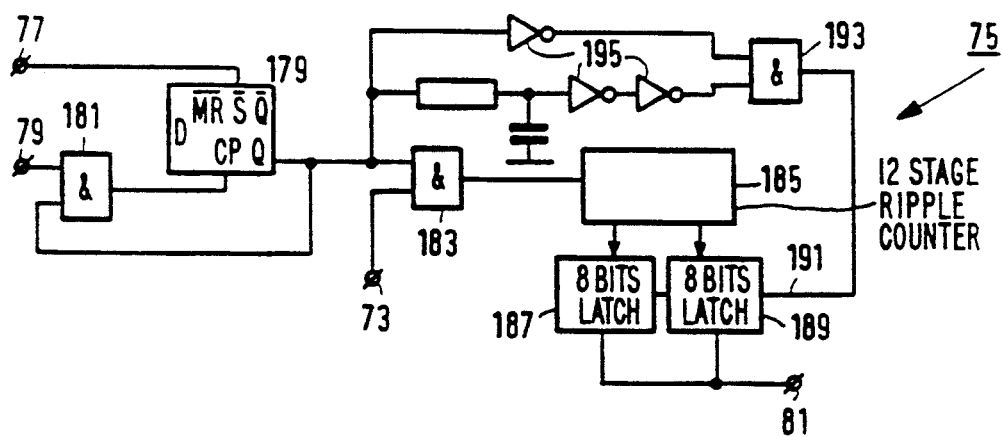

FIG. 12 is a block diagram of an embodiment of the counter 75. This circuit comprises a count enable circuit comprising a flipflop 179 and an AND-gate 181 which are connected as shown. If a reset signal appears on the second input 77, this count enable circuit generates a count enable signal and if subsequently a counter stop signal 48 is received on the third input 79, the count enable signal is removed. The count enable signal is supplied to a first input of an AND-gate 183 having a second input connected to the first input 73 of the counter 75. If a count enable signal is present on the first input of the gate 183, the clock pulses supplied to its second input are supplied to a twelve-stage ripple counter 185 that counts them and provides the result to the inputs of two eight-bits latches 187,189 that latch the counted value at the moment the count enable signal is removed. To this end the control input 191 of the latches 187,189 is connected, via an AND-gate 193 and some inverters 195, to the output of the count enable circuit. The counted value is available as a digital signal on the output 81 of the counter 75.

In order to make the result of the measurement available in the form of an analog signal, the counter 75 is followed, as shown in FIG. 5, by an analog-to-digital converter 197 (comprising e.g. a circuit of the type ADDAC 80) and a band-pass filter 199 which may have a low cut-off frequency of 0.05 Hz and a high cut-off frequency of 4 Hz, thus covering the range of frequencies in which respiration signals occur. It is clear that another pass-band for the filter 199 may be necessary if other phenomena are to be observed with the aid of the device.

FIG. 5 also shows that some parts of the device are disposed inside the RF shield 16 whereas other parts are disposed outside this shield. The parts inside the RF shield (shown in the top half of FIG. 5) comprise the transmitter means 71,21, the receiver means 23,83,85, the converter 91 and the envelope detector 95 with its low pass filter 103. These are all analog parts that do not produce RF interference. The digital parts, such as the timer 61, the control means 101 and the counter 75, are located outside the RF shield 16. The parts inside the RF shield 16 are connected to the parts outside this shield by means of connecting lines 201 that block electrical RF signals, for example, fibre optic transmission lines. Such fibre optic transmission lines conventionally comprise a transmitter comprising a light-emitting diode for converting an electrical signal into a modulated light wave, a length of optical fibre and a receiver comprising a light-sensitive element for converting the modulated light wave back into an electrical signal. The connecting lines 201 can also be formed e.g. by electrical conductors in series with RF filters.

We claim:

1. A method for determining variations in the position of a movable object comprising the steps of:

1) generating clock pulses at a predetermined clock frequency $F_{CL}$ and a sequence of transmission start signals having a repetition frequency $F_R$ and transmitting a burst of ultrasonic waves having a frequency $F_{US}$ towards the object each time a transmission start signal has been generated;
2) starting counting clock pulses at a time that has a predetermined relationship with the time when a start signal is generated;
3) receiving ultrasonic waves having the frequency $F_{US}$ reflected by the object and forming an analog echo signal that represents the electrical equivalent of the received ultrasonic waves;
4) converting the analog echo signal into a digital echo signal comprising a sequence of echo pulses at a repetition frequency equal to the frequency $F_{US}$ of the ultrasonic waves;
5) generating a time-window that has a predetermined width;
6) determining whether a predetermined edge of an echo pulse occurs within the time-window;
7) setting the time for generating the next time-window at $1/F_R - 1/2F_{US}$ seconds after an echo pulse has occurred within the time-window or at an estimated value if no echo pulse has occurred within the time-window; and
8) stopping the counting of clock pulses on the occurrence of a predetermined edge of an echo pulse in the time-window;
   wherein the estimated value for the time for generating the next time-window is obtained by the steps of:
   a) detecting the envelope of the analog echo signal;
   b) determining the time $t_L$ when the level of the envelope exceeds a predetermined level; and
   c) setting the time for generating the next time-window at $1/F_R - 1/2F_{US}$ seconds after the time $t_L$ if no echo pulse has occurred within the time-window.

2. A method as claimed in claim 1, characterized in that, if no echo pulse has occurred within the time-window, the counting of clock pulses is stopped at the time $t_L$.

3. A device for determining variations in the position of a movable object, comprising:

1) a timer (61) for generating clock pulses at a predetermined clock frequency $F_{CL}$, a sequence of transmission start signals (31) having a repetition frequency $F_R$ and reset signals having the same repetition frequency $F_R$ and a predetermined phase relationship to the transmission start signals, the clock pulses, transmission start signals and reset signals being made available on first (63), second (65) and third outputs (67), respectively, of the timer;
2) transmitter means (71,21) having its input (69) connected to the second output (65) of the timer (61) for transmitting a burst of ultrasonic waves having a frequency $F_{US}$ towards the object upon reception of a transmission start signal (31);
3) receiver means (23,83,85) for receiving ultrasonic waves having the frequency $F_{US}$ reflected by the object and making available on its output (87) an analog echo signal (39) that represents the electrical equivalent of the received ultrasonic waves;
4) converter means (91) for converting the analog echo signal (39) into a digital echo signal (41) comprising a sequence of echo pulses (43) having a repetition frequency $F_{US}$ equal to the frequency of the ultrasonic waves, the converter means having an input (89) connected to the output (87) of the receiver means (23,83,85) and making available the digital echo signal on its output (97);

5) control means (101) for generating a time-window (51) that has a predetermined width, determining whether a predetermined edge of an echo pulse (43) occurs within the time-window, setting the time for generating the next time-window at $1/F_R-1/2F_{US}$ seconds after an echo pulse has occurred within the time-window or at an estimated value if no echo pulse has occurred within the time-window and generating a counter stop signal (48) on the occurrence of a predetermined edge of an echo pulse in the time-window, the control means having a first input (99) connected to the output (97) of the converter means (91) and an output (119) on which the counter step signal is made available; and 6) counter means (75) having a first input (73) connected to the first output of the timer (61), a second input (77) connected to the third output (67) of the timer and a third input (79) connected to the output (119) of the control means (101);

wherein estimating means are provided for determining the estimated value for the time generating the next time-window (51), said estimating means comprising an envelope detector (95) for detecting the envelope (45) of the analog echo signal (39) and a level detector (111) for determining the time $t_L$ when the level of the envelope exceeds a predetermined level, the control means (101) further comprising means (121,122) for setting the time for generating the next time-window at $1/F_R-1/2F_{US}$ seconds after the time $t_L$ if no echo pulse (43) has occurred within the time-window (51).

4. A device as claimed in claim 3, wherein the control means (101) is adapted to generate a counter stop signal (48) at the time $t_L$ if no echo pulse (43) has occurred within the time-window (51).

5. A magnetic resonance apparatus comprising magnetic field generating means (1) for generating magnetic fields in a measurement space located behind an RF shield (16) and also a device for determining variations in the position of a movable object in said space comprising:

1) a timer (61) for generating clock pulses at a predetermined clock frequency $F_{CL}$, a sequence of transmission start signals (31) having a repetition frequency $F_R$ and reset signals having the same repetition frequency $F_R$ and a predetermined phase relationship to the transmission start signals, the clock pulses, transmission start signals and reset signals being made available on first (63), second (65) and third outputs (67), respectively, of the timer;

2) transmitter means (71,21) having its input (69) connected to the second output (65) of the timer (61) for transmitting a burst of ultrasonic waves having a frequency $F_{US}$ towards the object upon reception of a transmission start signal (31);

3) receiver means (23,83,85) for receiving ultrasonic waves having the frequency $F_{US}$ reflected by the object and making available on its output (87) an analog echo signal (39) that represents the electrical equivalent of the received ultrasonic waves;

4) converter means (91) for converting the analog echo signal (39) into a digital echo signal (41) comprising a sequence of echo pulses (43) having a repetition frequency $F_{US}$ equal to the frequency of the ultrasonic waves, the converter means having an input (89) connected to the output (87) of the receiver means (23,83,85) and making available the digital echo signal on its output (97);

5) control means (101) for generating a time-window (51) that has a predetermined width, determining whether a predetermined edge of an echo pulse (43) occurs within the time-window, setting the time for generating the next time-window at $1/F_R-1/2F_{US}$ seconds after an echo pulse has occurred within the time-window or at an estimated value if no echo pulse has occurred within the time-window and generating a counter stop signal (48) on the occurrence of a predetermined edge of an echo pulse in the time-window, the control means having a first input (99) connected to the output (97) of the converter means (91) and an output (119) on which the counter stop signal is made available; and 6) counter means (75) having a first input (73) connected to the first output of the timer (61), a second input (77) connected to the third output (67) of the timer and a third input (79) connected to the output (119) of the control means (101);

wherein estimating means are provided for determining the estimated value for the time generating the next time-window (51), said estimating means comprising an envelope detector (95) for detecting the envelope (45) of the analog echo signal (39) and a level detector (111) for determining the time $t_L$ when the level of the envelope exceeds a predetermined level, the control means (101) further comprising means (121,122) for setting the time for generating the next time-window at $1/F_R-1/2F_{US}$ seconds after the time $t_L$ if no echo pulse (43) has occurred within the time-window (51); and wherein parts of the device, including the transmitter means (21,71), the receiver means (23,83,85) and the converter means (91) are located behind the RF shield (16), the parts of the device which are located behind the RF shield being connected to parts of the device located outside the RF shield by means of connecting lines (201) that block electrical RF signals.

* * * * *